United States Patent
Widlund et al.

[11] Patent Number: 5,382,467
[45] Date of Patent: Jan. 17, 1995

[54] RESILIENT BODY AND A METHOD FOR ITS MANUFACTURE

[75] Inventors: Urban Widlund, Mölnlycke; Roy Hansson, Mölndal, all of Sweden

[73] Assignee: Molnlycke AB, Goteborg, Sweden

[21] Appl. No.: 862,531

[22] PCT Filed: Dec. 20, 1990

[86] PCT No.: PCT/SE90/00860
§ 371 Date: Jun. 22, 1992
§ 102(e) Date: Jun. 22, 1992

[87] PCT Pub. No.: WO91/09581
PCT Pub. Date: Jul. 11, 1991

[30] Foreign Application Priority Data
Dec. 21, 1989 [SE] Sweden .......................... 8904314-5

[51] Int. Cl.6 .......................................... A61F 13/15
[52] U.S. Cl. .......................................... 428/284; 428/72; 428/73; 428/105; 428/117; 428/158; 428/178; 156/160; 156/161; 156/163; 156/164; 156/494; 156/467; 156/552; 604/385.1; 604/385.2
[58] Field of Search ............... 604/369, 385.1, 385.2; 428/72, 73, 105, 117, 158, 178, 284; 156/166, 161, 163, 164, 494, 552, 141

[56] References Cited
U.S. PATENT DOCUMENTS

| | | | |
|---|---|---|---|
| 4,360,021 | 11/1982 | Stima | 128/287 |
| 4,655,760 | 4/1987 | Morman et al. | 604/85 |
| 4,994,053 | 2/1991 | Lang | 604/367 |

Primary Examiner—Patrick J. Ryan
Assistant Examiner—Richard Weisberger
Attorney, Agent, or Firm—Young & Thompson

[57] ABSTRACT

The present invention relates to a resilient body which includes two thin layers (1, 6) of flexible material to which intermediate elastic threads (2, 3, 5) or bands are fastened in a stretched state and disposed in a regular, net-like pattern, and bodies (4) of soft material are disposed between the two layers (1, 6) in at least some of the meshes of the net formed by the elastic threads. These bodies have smaller dimensions than the meshes, so as to permit total or partial contraction of the stretched or tensioned elastic threads. The bodies also have an intrinsic stiffness such as to substantially retain their shape upon contraction of the elastic threads. The invention also relates to a method for manufacturing the inventive resilient body.

10 Claims, 2 Drawing Sheets

RESILIENT BODY AND A METHOD FOR ITS MANUFACTURE

FIELD OF THE INVENTION

The present invention relates to a resilient body including two thin layers of flexible material, of which at least one layer is elasticated, intended particularly for use in diapers and incontinence guards. The invention also relates to a method for the manufacture of the resilient body.

BACKGROUND OF THE INVENTION

The development of materials used in the absorption pads or bodies of incontinence guards and diapers have made it possible at present times to configure different parts of the absorbent pads with mutually different properties, i.e. by the admixture of so-called superabsorbents, and thereby, for instance, enable the flow of liquid in an absorbent pad to be controlled in a desired manner. The use of superabsorbents also enables absorbent pads to be given smaller dimensions and nevertheless exhibit a satisfactory absorption capacity.

U.S. Pat. No. 4,360,021 discloses an absorbent article having a multiplicity of bodies of superabsorbent material arranged in separate pockets between a cover sheet and a backing sheet. However, none of the sheets is elasticated in order to improve the fit of the article.

Leakage in modern diapers or incontinence guards is often because instead of being absorbed into the absorbent pad the liquid runs along the surface of the pad casing layer which lies nearest the skin and thereafter leaks from the diapers or incontinence guards. Such leakage may be due to the formation of folds or pleats at this surface when putting on the diaper or incontinence guard, these folds or pleats functioning as flow channels and therewith restricting the desired-dispersion of liquid.

Accordingly, strenuous efforts have been made in recent times within this field to improve the body fit of diapers and incontinence guards, so as to prevent undesirable deformation of the diaper or guard when it is put on. One conventional method of enhancing body fit is to provide the diaper or incontinence guard with elastication. Present day diapers and incontinence guards are therefore often provided with leg and waist elastication in order to achieve tightness along the edges of the diaper or incontinence guard. It has also been suggested that elastication is applied to the casing surrounding the absorbent pad, such that the casing will be given an appropriate form, for instance a basin-like configuration, so that the diaper or incontinence guard can be put-on correctly and so that undesirable deformation is prevented.

Another example of a diaper or an incontinence guard provided with elastication is disclosed in U.S. Pat. No. 4,655,760, in which one of the two casing layers enclosing the absorbent body comprises an elasticated, gathered portion in order to improve fit and enhance liquid retention. Expansion and contraction of the elasticated casing layer is permitted by the fact that the absorbent body is not bonded to this layer.

Although the provision of such elastication will impart improved properties to a diaper or an incontinence guard, the stiffness of the absorbent pad makes it difficult to utilize the elasticity of the elastication to the full and to provide elasticitiy to all those parts of a diaper or an incontinence guard desirable.

U.S. Pat. No. 4,699,621 teaches a diaper in which the elastic properties of the diaper are achieved by enclosing an absorbent pad in a conventional casing, i.e. a casing comprising an outer layer of liquid-impermeable material and an inner layer of liquid-permeable material and is loosely fastened to an outer layer of elastic material in a manner such that this attachment will only influence the elastic properties of the outer layer to an insignificant extent. With this construction an attempt has been made to solve the problem of the influence of the absorbent body on the properties of the elastic, by producing the elastic properties of the article with the aid of a separate element separated from the absorbent pad. However, it is difficult, even with this construction, to achieve desired abutment of the absorbent pad against the skin of the user. due to the fact that the relatively rigid absorbent pad is unable to conform completely to the body contours.

SUMMARY OF THE INVENTION

The object of the present invention is to provide a resilient body which can follow the contours of a surface of varying curvature, and which includes a material having a given intrinsic stiffness so as to impart desired shape stability to the resilient body, this material possibly having absorbent properties.

Accordingly, the inventive resilient body is characterized in that it includes two thin layers of flexible material, of which at least one layer is elasticated, in that material bodies are disposed in a given pattern between the layers and placed in mutually spaced relationship in the stretched state of the elasticated layer or layers, in that the layers are mutually joined at parts which lie between the material bodies, and in that the material bodies have an intrinsic stiffness such as to substantially retain their form when the elasticated layer or layers contracts or contract from their streched to at least a substantially relaxed state. In the inventive resilient body, when the elasticated layer or layers contracts/contract that part of the two-layer, flexible material which lies outside each body will bend around the periphery of the stiffer material body. Desired shape stability of the resilient body can be achieved in that bodies, which are disposed adjacent to one another, will come into peripheral contact with each other after contraction, provided that the tension in the elasticated layer is sufficiently high. The elasticity can thus be utilized completely in such a resilient body in parts which lie outside the material bodies. Furthermore, because of their small size, these bodies will not prevent the resilient body from conforming to the body contours of the wearer of a diaper or an incontinence guard provided with such a resilient body. The material bodies can be given absorbent properties, by manufacturing the bodies from an absorbent material either completely or partially. By constructing an absorbent article from mutually adjacent, separate absorbent bodies of small dimensions, there is naturally obtained an article which is much more flexible than an article with a single absorbent body of the same material. Since the small bodies are mutually separated, no through-passing channels can form when the inventive resilient body is deformed. Furthermore, the risk of lumping is reduced in an absorbent body which comprises a plurality of small, mutually separate bodies of absorbent material.

In accordance with a first embodiment of the invention, elastication of the flexible layers is achieved by forming one or both layers from an elastic plastic material, while in a second embodiment elastication is achieved by fastening stretched elastic threads or bands between two flexible but inelastic layers.

The present invention also relates to a method for manufacturing such a resilient body, this method being characterized in that elastic threads are applied in a given net-like pattern and lengthened or stretched to a given extent from a tensionless state on a first material web of a first flexible material and attached to said web; in that material bodies of smaller dimensions than the meshes of the elastic thread network are placed on the first material web in a given pattern so that subsequent to positioning said bodies and said elastic threads the bodies will be located in meshes of the net formed by said threads; in that a second material web of a second flexible material is thereafter placed on top of the unit consisting of the first material web, the elastic threads and the bodies, and is fastened at least to the threads; and in that the elastic threads are then cut along the outer edges of the thus formed composite material web, and said threads contract and the material webs fold around the peripheries of said bodies.

BRIEF DESCRIPTION OF THE DRAWINGS

The invention will now be described in more detail with reference to the accompanying drawings, which illustrate a preferred exemplifying embodiment of an inventive resilient body and a method step in the manufacture of this resilient body, in which drawings

DETAILED DESCRIPTION OF THE INVENTION

A preferred method for manufacturing the inventive resilient body will now be described with reference to FIG. 1.

Elastic threads are applied to a first material web of a first flexible material 1 and fastened to said web in a suitable manner to form a given net-like pattern. In the preferred embodiment, the first flexible material 1 comprises a liquid impervious plastic material of the kind conventionally used in the manufacture of absorbent disposable articles, such as diapers or incontinence guards. In the present case there has been formed a pattern which is suitable to enable triangular parts to be cut from the final product, in the form of a continuous, composite material web. It will be understood, however, that the threads can be applied in other patterns, depending on the shape of the product in which the resilient body produced shall be used.

Figure 1:
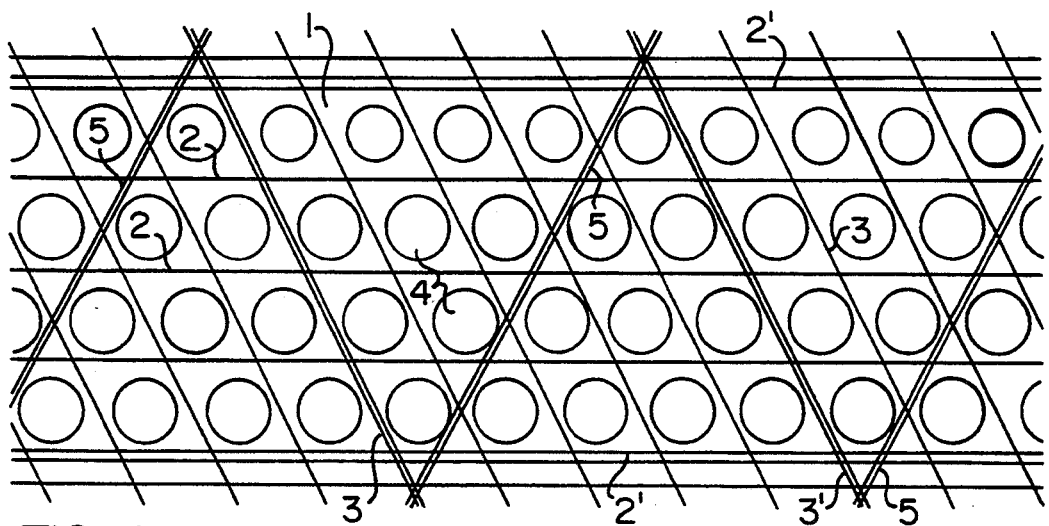
FIG. 1 illustrates an exemplifying embodiment of an inventive resilient body during one stage of its manufacture.

The pattern illustrated in FIG. 1 is comprised of longitudinally extending elastic threads 2 and transversely extending elastic threads 3, which intersect the longitudinally extending threads at an angle other than 90°. The threads 2, 3 therewith form a net-like pattern having rhomboidic meshes. These threads are also stretched, or tensioned, i.e. they are stretched from their relaxed states when applied to the web. The stretched elastic threads can be applied to the web with the aid of any of the known devices used in this field of the art for this purpose. Circular bodies 4 made of soft material having a given intrinsic stiffness are then placed in a suitable fashion in each of the rhomboidic meshes of the net 2, 3 and fastened to the web material. This can be effected, for instance, by punching these bodies, with the aid of a hole punch or the like, from a mat which has the same width as the web of the first flexible material 1 and which is placed immediately above said web. Other methods of applying these bodies are conceivable of course; for instance, the bodies can be formed in separate moulds and then applied to the web directly or in rows, if it is wished to avoid wastage of material or when bodies of separate materials or of differing properties shall be included in the pattern.

As will be seen from FIG. 1, the pattern also includes elastic threads 5 which extend across the web and which are inclined to the transverse direction at mutually the same angle as but in different directions to the threads 3. These threads 5 comprise two-ply elastic threads. The two outermost, longitudinally extending threads 2' also comprise twin-ply threads, as do also the transversely extending threads 3' which intersect the threads 5 immediately outside the outer limitations of the material web.

The bodies may also be applied prior to attaching the elastic threads, wherein the elastic threads are then placed in the spaces between the bodies in an intended pattern.

Subsequent to mounting elastic threads and material bodies on the first web and attaching said threads and bodies in some suitable fashion, a second web of a second flexible material 6 is placed on the thus formed unit consisting of the first web, the threads and the bodies. In the illustrated case, the second flexible material consists of liquid-permeable material of the kind typically used as an inner surface layer or sheet of a diaper or an incontinence guard.

The resultant resilient body with elastic threads 2, 3 and 5 and material bodies 4 is then cut into triangular parts, by cutting between the two-ply threads 3', 5 and by also cutting the ends of the threads that lie outside the outer edges of the web.

Figure 2:
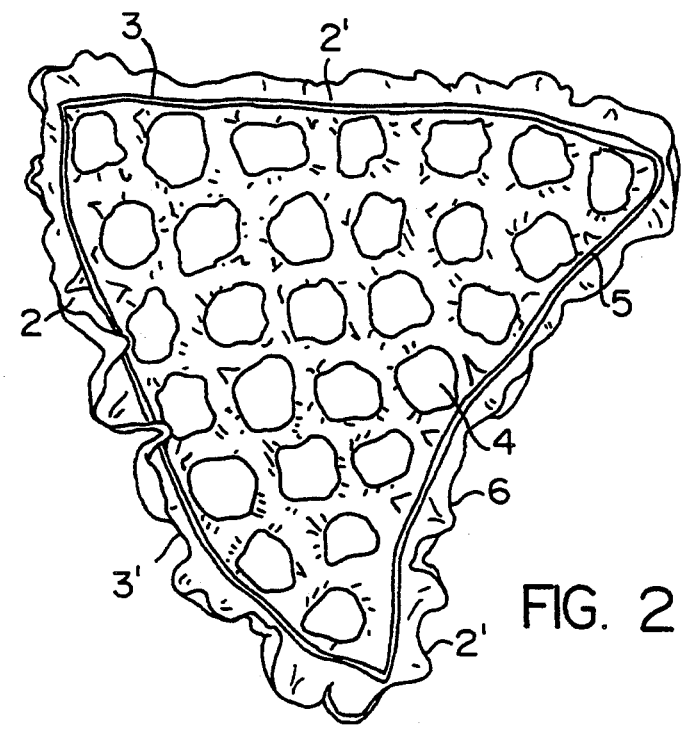
FIG. 2 illustrates the upper side of a triangular part of an inventive resilient body in a relaxed state.
Figure 3:
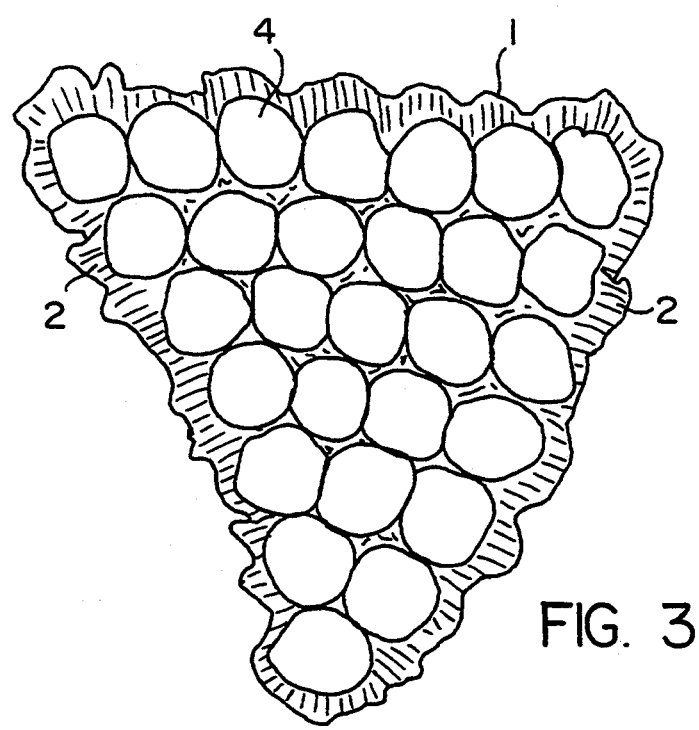
FIG. 3 shows the underside of the part illustrated in FIG. 2.

In the case of the preferred embodiment, gluing is used as the method of attachment. As mentioned in the aforegoing, the flexible material webs are also fastened to the threads, the bodies and to one another. A triangular part constructed in the same way is illustrated in FIGS. 2 and 3, wherein in FIG. 2 the liquid-permeable layer 6 faces towards the viewer, whereas in FIG. 3, the liquid-impermeable layer 1 faces towards the viewer.

The triangular part illustrated in these Figures differs from the parts indicated in FIG. 1, in that the net pattern includes more meshes. Thus, the pattern in FIG. 1 includes four horizontal rows of material bodies, whereas the resilient body illustrated in FIGS. 2 and 3 includes seven rows of horizontal bodies. It is evident from these Figures that contraction of the elastic threads to a relaxed state subsequent to cutting-out the triangular parts will result in folding of the flexible layers 1, 6 around the periphery of the material bodies. Provided that the threads have been stretched to sufficient tension, the flexible material will be drawn in over the upper side of the bodies 4, which is defined as the side facing towards the viewers of FIG. 2, so as to form ridges 7 of folded, flexible material and elastic threads on the upper side, around the periphery of the bodies. The bodies are therewith drawn towards one another, so that the parts of the flexible layers 1, 6 drawn up around the sides of respective bodies 4 will lie in abutment with one another along parts of the periphery of respective bodies, as illustrated in FIG. 3.

The bodies are made of a soft material having an intrinsic rigidity which is sufficiently large to prevent the bodies from being deformed, or from being deformed more than slightly when the elastic threads contract. In the case of the preferred embodiment, the bodies are formed from absorbent material, such as cellulose fluff or wadding, with additions of so-called superabsorbents. Binding fibres can be added, for the purpose of imparting desired stiffness to the small absorbent bodies.

Because the parts of the layers 1, 6 drawn up around the bodies 4 lie against corresponding parts of adjacent bodies, there is formed a shape-stable unit in the contracted state of the threads 2, 3, 4. This unit has a very low resistance to bending in the direction towards the viewer of FIG. 2, since the ridges 7 form bending hinges in this direction. When the unit illustrated in FIGS. 2 and 3 is included as part of a diaper or the like, the unit can therefore be adapted very readily to the body contours of the wearer when the upper side of the unit of FIG. 2 is placed nearest the skin. When bending in the other direction, the under edges of the bodies act as bending hinges and bending will cause the ridges 7 to unfold against the action of the spring forces exerted by at least the obliquely extending threads. Since the force generated by such bending acts on a small part of the periphery of the bodies, said bending will result in at least local deformation of the bodies.

Figure 4:
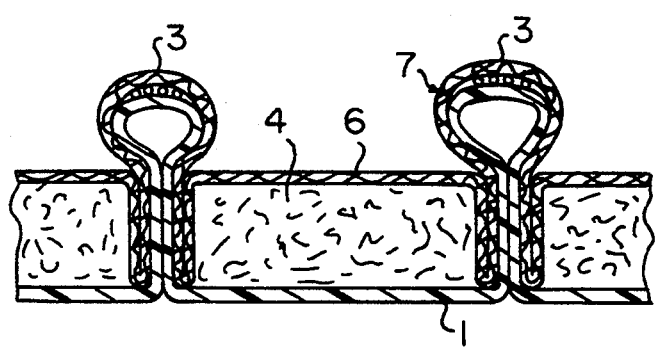
FIG. 4 is a sectional view taken on the line IV—IV in FIG. 3.
Figure 5:
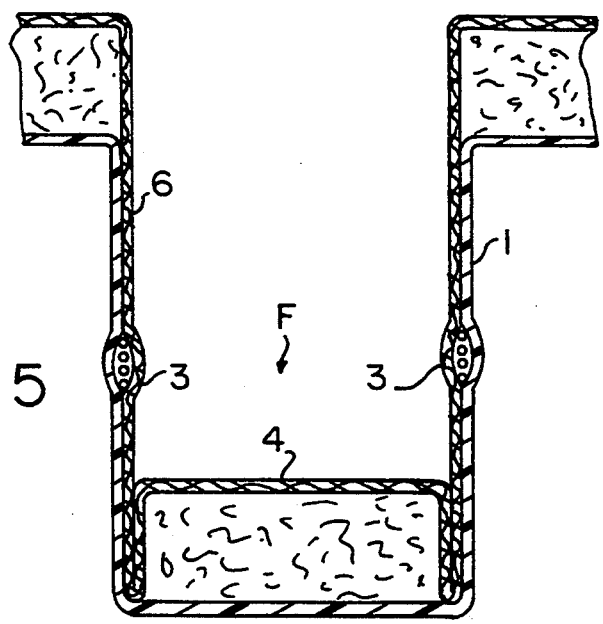
FIG. 5 is a sectional view corresponding to FIG. 4 illustrating a downwardly pressed material body.

FIG. 4 is a schematic illustration on a larger scale of a part cut from the triangular part of the inventive resilient body and shows said part. As will be seen from this Figure, and from FIG. 2, the four ridges 7 form the walls of a container, the bottom of which is formed by the material body 4, said ridges 7 extending around the periphery of each material body 4 and consisting of elastic threads and folded parts of the mutually joined layers 1, 6. When the bottom of this container is pressed downwards by a force F, the container walls can take the position illustrated in FIG. 5, against the action of the spring effect of the elastic threads, therewith greatly increasing the container volume. FIG. 5 illustrates the maximum extent to which the container walls can be moved downwards relative to adjacent material bodies, and it is assumed therewith that the material bodies lying around the activated or influenced body are not activated or influenced, said bodies being six in number in the illustrated net pattern.

The invention thus provides a resilient body whose elastic properties can be varied by selection of net pattern and tensioning of the elastic threads, and which is shape-stable despite its elasticity. When the resilient body is used in diapers or incontinence guards, the ridges formed by elastic threads and folded layer material form barriers against liquid dispersion from the containers formed by said ridges and bodies, and when these bodies consist of absorbent material, the absorption capacity of said bodies can be utilized to the full when the "container" is filled by liquid that overflows from an adjacent "container".

The triangular part described with reference to the illustrated embodiments of the invention can be used advantageously as a back sheet of a diaper or an incontinence guard. The threads 2' form waist elastication and the threads 3', 5 form leg elastication. These threads may then advantageously comprise several threads or plies or an elastic band. Since present day techniques enable the front piece of a diaper or an incontinence guard to have an absorption capacity which will enable it to absorb all liquid discharged alone, the primary purpose of the back piece is to prevent liquid which flows for some reason or other from the front piece to the back piece from spreading to the edges of the back piece. This purpose is achieved by the presence of the aforesaid liquid dispersion barriers. Thus, in principle the bodies present in the back piece need not be absorbent. It is preferred, however, to give absorbent properties to at least those bodies located nearest the front piece.

The back piece of a diaper or an incontinence guard is also intended to handle the discharge of faeces, by preventing spreading of the faeces to the edges. Because of the inventive construction of dispersion barriers and "expandable" containers, the inventive resilient body is well suited for this purpose. Since the faeces of diaper-wearing children are liable to contain a large quantity of liquid, the majority of the material bodies of the diaper back piece should possess absorbent properties.

Since the liquid dispersion aspects of the inventive resilient body are of subordinate significance when the resilient body is used as a back piece in an incontinence guard, the liquid-permeable layer in such cases can be permitted to fold or pleat on the upper side of the body. In this application, it is therefore sufficient to attach the permeable layer to solely the elastic threads.

The inventive resilient body can also be given different elastic properties in mutually different parts, for instance, by varying the tension in the elastic threads. Naturally, different elastic properties can also be achieved by using in given parts of said resilient body, material bodies whose dimensions are larger than the dimensions of the net meshes and by fastening these material bodies to both the elastic threads and the underlying material web.

The inventive resilient body can also be elasticated in other ways than by using elastic threads or bands. For instance, one or both of the flexible layers 1 and 6 may consist of an elastic material or a plastic film having a so-called elastic memory, for instance different qualities of EXXON- or EXTRAFLEX-. These plastic films can be greatly extended or stretched under plastic deformation, so that their extension will remain subsequent to removing the load causing such extension, but which return to their original size when heated and therewith have elastic properties within the range of their original size and their extended size. Elastic threads are preferred, however, when there is desired a resilient body which has elastic properties in several directions. It is, of course, conceivable to use bands of memory material instead of elastic threads.

It will be understood that the described inventive resilient body and the described method for its manufacture can be modified in many ways within the scope of the invention. For instance, the bodies may have a form other than circular, for instance rectangular, rhomboidic, etc., and may be placed in solely some of the meshes. Furthermore, the net pattern may have any configuration whatsoever, depending on the product in which the resilient body is to be used, and may, for instance, comprise solely threads which extend in both the transverse and longitudinal directions and which intersect one another at acute angles so that parts of hourglass configuration can be cut from the resilient body. Similarly, the use of an inventive resilient body is not restricted to products of the aforedescribed kind. The invention is therefore only restricted by the content of the following claims.

We claim:

1. A resilient body for use in diapers and incontinence guards comprising: two layers (1, 6) of flexible material, of which at least one layer is elasticated, material bodies (4) arranged in a given pattern between the layers (1, 6) and attached mutually spaced from one another in a stretched state of said at least one elasticated layer; said layers being mutually joined at parts located between the bodies; and said bodies having an intrinsic stiffness such that said bodies will substantially retain their shape when said at least one elasticated layer contracts from a stretched state to at least a substantially relaxed state.

2. A resilient body according to claim 1, wherein at least one of the flexible layers (1, 6) comprises an elastic plastic material.

3. A resilient body according to claim 1, wherein elastication is obtained by means of elastic threads (2, 3, 5) located between the layers (1, 6) and attached to said layers while in a stretched state, said elastic threads being disposed in a repeated, mesh-like pattern so as to form a network, whereby at least some of the meshes of the formed network of elastic threads contain material bodies (4) having an intrinsic stiffness such that said bodies will substantially retain their shape subsequent to contraction of the elastic threads from a stretched state to a completely or partially relaxed state.

4. A resilient body according to claim 1, wherein the bodies (4) are made of cellulose fluff.

5. A resilient body according to claim 1, wherein the bodies (4) are made of wadding admixed with superabsorbent material.

6. A resilient body according to claim 1, wherein the two layers (1, 6) of flexible material are attached to the bodies and to each other.

7. A resilient body according to claim 1, wherein one (1) of the layers of flexible material comprises a liquid-impermeable material, whereas the other layer (6) comprises a liquid-permeable material.

8. A method for manufacturing a resilient body for use in diapers and incontinence guards, which comprises: applying elastic threads in a given mesh-like pattern and extending said threads through a given distance from a tensionless state on a first material web of a first flexible material, and fastening said threads to said web so as to form a network; placing material bodies of dimensions smaller than the meshes in the pattern formed by the elastic threads on the first material web in a given pattern, so that subsequent to applying the bodies and the threads said bodies will be located in meshes on the network formed by said threads; applying a second material web of a second flexible material on top of the unit comprising said first web, said elastic threads and said bodies, and fastening said second web to at least the elastic threads; and then cutting the elastic threads along outer edges of the formed, composite material web, whereupon said threads contract and the webs fold around the peripheries of the bodies.

9. A method according to claim 8, further including: coating the first material web with glue prior to mounting elastic threads and material bodies thereon, and coating the second material web with glue prior to joining said second web to said first web, threads and material bodies.

10. A resilient body according to claim 4, wherein the bodies are admixed with superabsorbent material.

* * * * *